United States Patent
Pack et al.

(10) Patent No.: US 10,034,675 B2
(45) Date of Patent: Jul. 31, 2018

(54) SYSTEMS AND METHODS FOR PRE-OPERATIVE PLANNING AND PRECISE BONE TUNNEL PLACEMENT FOR LIGAMENT RECONSTRUCTION

(71) Applicant: CUREXO TECHNOLOGY CORPORATION, Fremont, CA (US)

(72) Inventors: Timothy J. Pack, Fremont, CA (US); Youngbae Park, Fremont, CA (US)

(73) Assignee: THINK SURGICAL, INC., Fremont, CA (US)

( * ) Notice: Subject to any disclaimer, the term of this patent is extended or adjusted under 35 U.S.C. 154(b) by 225 days.

(21) Appl. No.: 14/776,093

(22) PCT Filed: Mar. 13, 2014

(86) PCT No.: PCT/US2014/025965
§ 371 (c)(1),
(2) Date: Sep. 14, 2015

(87) PCT Pub. No.: WO2014/160170
PCT Pub. Date: Oct. 2, 2014

(65) Prior Publication Data
US 2016/0030063 A1     Feb. 4, 2016

Related U.S. Application Data

(60) Provisional application No. 61/780,904, filed on Mar. 13, 2013.

(51) Int. Cl.
*A61B 17/17*     (2006.01)
*A61B 34/20*     (2016.01)
(Continued)

(52) U.S. Cl.
CPC ...... *A61B 17/1714* (2013.01); *A61B 17/1764* (2013.01); *A61B 34/10* (2016.02);
(Continued)

(58) Field of Classification Search
CPC . A61B 17/1714; A61B 17/1703; A61B 34/10; A61B 2034/107
See application file for complete search history.

(56) References Cited

U.S. PATENT DOCUMENTS 2,693,794 A * 11/1954 Neville ............... A61M 5/52
128/877
4,136,858 A *  1/1979 Petersen ............. A61G 13/12
5/624

(Continued)

FOREIGN PATENT DOCUMENTS

WO     2007092841 A2     8/2007

OTHER PUBLICATIONS

Burkart, Andreas et al. "Precision of ACL Tunnel Placement Using Traditional and Robotic Techniques", Computer Aided Surgery; pp. 270-278, (2001); online Journal homepage: http://www.tandfonline.com/loi/icsu20;http://dx.doi.org/10.3109/10929080109146092.

(Continued)

*Primary Examiner* — Christian Sevilla
(74) *Attorney, Agent, or Firm* — Avery N. Goldstein; Blue Filament Law, PLLC

(57) ABSTRACT

Methods and systems to optimize ligament reconstruction surgical outcomes by enabling bone tunnel(s) to be precisely and optimally placed through the use of pre-operative planning systems coupled with precision control bone evacuation machines, such as robotic drills are provided. The methods generally include receiving and processing scan data of a patient's bone(s); pre-determining the optimal tunnel placement parameter(s) with the scan data; placing registration marker(s) on the patient's bone(s) percutaneously; and creating a tunnel in the patient's bone(s) with a system coupled to receive and execute according to the pre-determined optimal tunnel placement parameter(s).

18 Claims, 4 Drawing Sheets

(51) Int. Cl.
*A61B 34/30* (2016.01)
*A61B 34/10* (2016.01)
(52) U.S. Cl.
CPC .............. *A61B 34/20* (2016.02); *A61B 34/30* (2016.02); *A61B 2034/105* (2016.02)

(56) References Cited

U.S. PATENT DOCUMENTS

| | | | | |
|---|---|---|---|---|
| 4,545,573 | A * | 10/1985 | Murphy | A61G 13/12 269/131 |
| 6,701,174 | B1 | 3/2004 | Krause et al. | |
| 6,725,082 | B2 | 4/2004 | Sati et al. | |
| 2005/0149054 | A1 * | 7/2005 | Gorek | A61B 17/1757 606/104 |
| 2006/0161052 | A1 * | 7/2006 | Colombet | A61B 5/064 600/300 |
| 2010/0275377 | A1 * | 11/2010 | West | A61F 5/3776 5/621 |
| 2010/0298894 | A1 * | 11/2010 | Bojarski | A61B 17/1764 606/86 R |
| 2011/0015649 | A1 * | 1/2011 | Anvari | A61B 34/30 606/130 |
| 2011/0047706 | A1 * | 3/2011 | Hiebert | A61F 5/3769 5/623 |
| 2011/0144650 | A1 | 6/2011 | Re et al. | |
| 2011/0245951 | A1 * | 10/2011 | Gantes | A61C 1/084 700/98 |
| 2012/0041446 | A1 | 2/2012 | Wong et al. | |
| 2012/0046668 | A1 * | 2/2012 | Gantes | A61C 1/084 606/130 |
| 2013/0060278 | A1 | 3/2013 | Bozung et al. | |

OTHER PUBLICATIONS

Petermann, Joerg et al. "Computer-Assisted Planning and Robot-Assisted Surgery in Anterior Cruciate Ligament Reconstruction", Operative Techniques in Orthopaedics, vol. 10, No. 1 (Jan. 2000); pp. 50-55.

European Extended Search Report dated Sep. 30, 2016 for European Application No. EP 14772790.3, filed Oct. 9, 2015, based on International Application PCT/US2014/025965.

International Search Report dated Aug. 25, 2014 for International Application No. PCT/US2014/025965 filed Mar. 13, 2014.

* cited by examiner

PRE PLAN TUNNEL PLACEMENT IN ORTHO-PLANNING SOFTWARE

PLAN TUNNEL 1 - TIBIAL TUNNEL

PLAN TUNNEL 2 - FEMORAL TUNNEL

SYSTEMS AND METHODS FOR PRE-OPERATIVE PLANNING AND PRECISE BONE TUNNEL PLACEMENT FOR LIGAMENT RECONSTRUCTION

CROSS-REFERENCE TO RELATED APPLICATION

This application claims priority of U.S. Provisional Patent Application Ser. No. 61/780,904 filed Mar. 13, 2013, which is incorporated herein by reference.

FIELD OF THE INVENTION

This invention relates generally to the ligament reconstruction, and more specifically to a new and useful system and method for pre-operative planning and precise bone tunnel placement in orthopedic surgery.

BACKGROUND OF THE INVENTION

Rupture of the anterior cruciate ligament (ACL) is one of the most frequent injuries to the knee joint in the young. ACL reconstruction is a major orthopedic procedure most often performed in the younger adult population. Early stabilization of the knee joint by ACL reconstruction also decreases the risk of injury to other important structures.

The biggest challenge in ACL reconstruction is typically the exact placement of drilled bone tunnels. When poorly placed, bone tunnels significantly affect the outcome of surgery. Outcomes affected by poor tunnel placement include restricted range of motion, knee joint instability, reaction of the synovium in the knee, pain, impingement and potential graft failure with lesion development.

Precisely placed tunnels are difficult to achieve through current surgical methods. While ACL reconstruction is predominately performed arthroscopically, arthroscopy does not allow the surgeon to gain a complete 3D view of important anatomical structures, particularly in the anteroposterior direction. Large incisions are often required to provide surgeons adequate access to landmarks and/or drill angles. Further, as ACL reconstructions require a high learning curve to master, attainable only from high volumes and extensive experience, ACL reconstructions are most often performed by under experienced orthopedic surgeons. It is estimated that up to 20% of ACL grafts fail due to impingement or poor tunnel placement.

Thus, there exists a need for a more reliable method for a surgeon to precisely place bone tunnels for not just ACL reconstruction, but any ligament reconstruction or other orthopedic surgery minimally invasively. Inventions described in this application provide such a new and useful system and method.

SUMMARY OF THE INVENTION

Methods and systems to optimize ligament reconstruction surgical outcomes by enabling bone tunnel(s) to be precisely and optimally placed through the use of pre-operative planning systems coupled with precision control bone evacuation machines, such as robotic drills are provided. The methods generally include the steps of receiving and processing scan data of a bone or a joint inclusive of the bone; pre-determining the optimal tunnel placement parameter(s) with the scan data; and creating a tunnel in the bone of the subject according to the pre-determined tunnel placement parameter. A robotic system is provided for planning and placing such tunnels into bone for ligature replacement.

DETAILED DESCRIPTION OF THE INVENTION

This application describes methods and systems to optimize ligament reconstruction surgical outcomes by enabling bone tunnels to be precisely and optimally placed through the use of pre-operative planning systems coupled with precision control bone evacuation machines, such as robotic drills. The inventions described herein also represents methods and systems to improve ligament graft survival by enabling precisely matched bone tunnel(s) to be placed minimally invasively, which otherwise would only be possible through open surgeries or surgeries requiring significantly larger incisions. Other advantages of the inventions disclosed herein include a stable platform for bone cutting processes to be performed homogeneously; means to create bone tunnels of customizable shapes or sizes to accommodate complex ligament grafts such as the multiple tunnels required for a double or triple bundle ligament graft; reduction in surgical time required to perform a ligament reconstruction procedure; and ability for an orthopedic surgeon to improvise the use of described inventions to make intraoperative decisions based on the pre-operative planning systems disclosed in this application. The following description of the preferred embodiments of the invention is not intended to limit the invention to these preferred embodiments, but rather to enable any person skilled in the art to make and use this invention.

Figure 1:
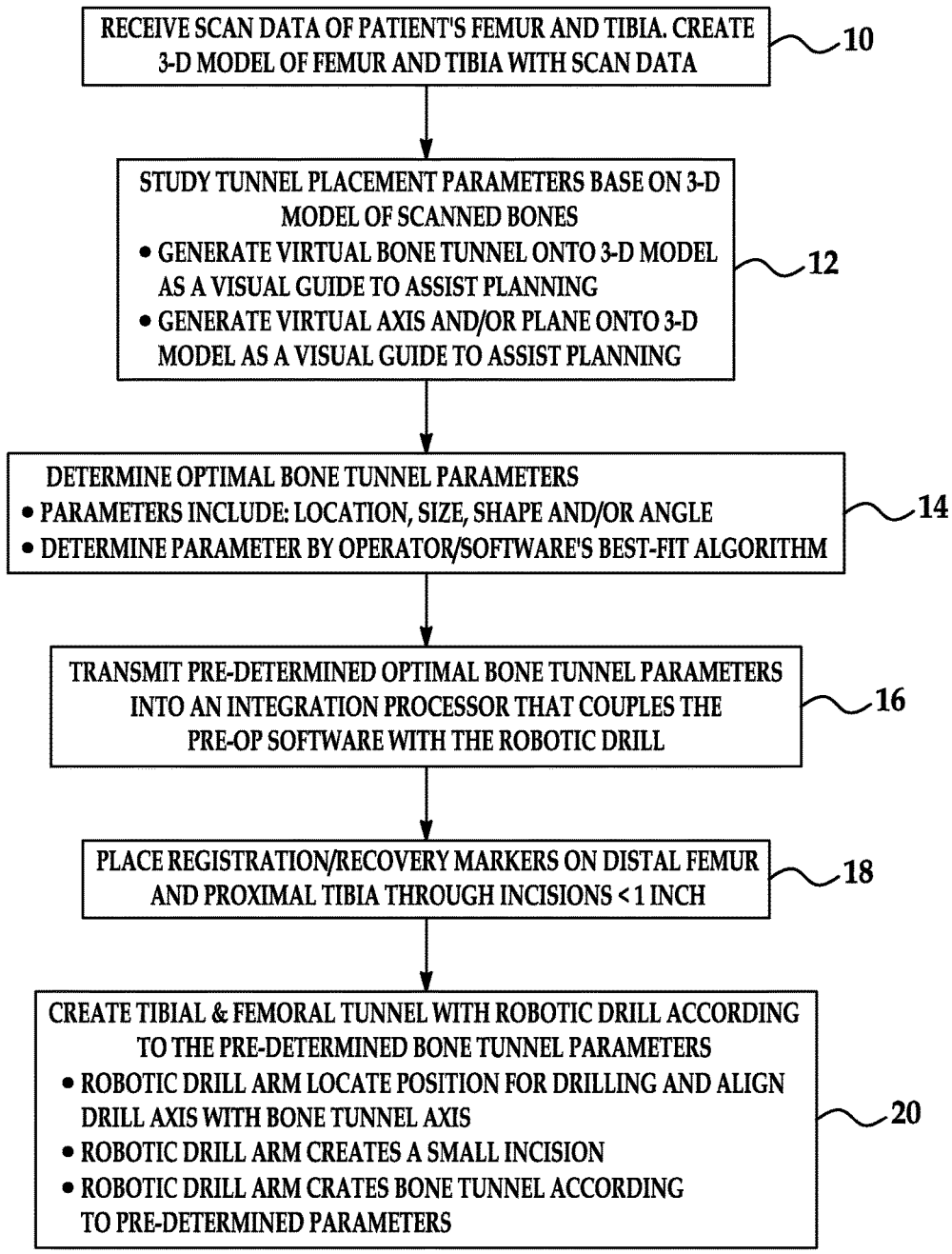
FIG. 1 is a flowchart showing a preferred method for creating a precise bone tunnel through pre-operative planning and robotics.

FIG. 1 illustrates a flow chart describing a preferred method and system for minimally invasive robotic ACL reconstruction by creating a precise bone tunnel through coupling pre-operative planning systems with robotics drilling. In one preferred embodiment, the method includes the steps of creating a 3-D model of the femur and tibia 10, studying a plurality of tunnel placement parameters via a pre-operative planning software 12, determining the optimal tunnel placement parameters either through 3-D simulations selected by the operator or through best-fit algorithm prescribed by the software 14, transmitting and processing said parameters into an integration processor coupling the pre-operative planning software and a robotics bone drill 16, placing registration markers on the distal femur and proximal tibia 18, and creating the femoral and tibial tunnels with the robotics drill to precisely match the most optimal bone tunnel parameters pre-determined before the procedure through a minimally invasive incision 20.

In some embodiments, step 10 which recites creating a 3-D model of the femur and tibia may include the steps of receiving scan data of patient's femur and tibia and importing virtual 3-D model of scanned bones generated from said data into a pre-operative planning software.

Figure 2A:
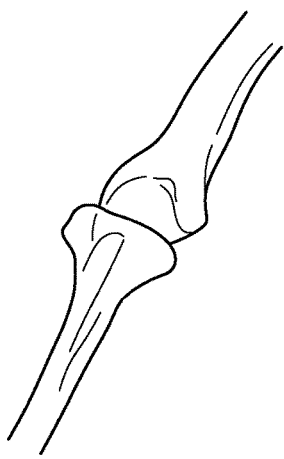
FIGS. 2A-C shows steps of the pre-operative tunnel placement software in planning (FIG. 2A), tibial tunnel placement (FIG. 2B), and femoral tunnel placement (FIG. 2C)
Figure 2B:
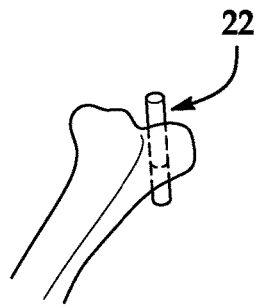
Figure 2C:
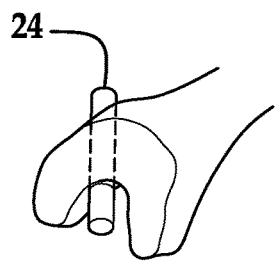

In some embodiments, the method includes step 12 which recites studying a plurality of tunnel placement parameters via pre-operative planning software, FIG. 2A. This step may further include analyzing tunnel placement parameters with the pre-op planning software. The ortho-planning software allows for viewing and analysis of various tunnel sizes, as shown in FIG. 2A. Optimal tunnel placement parameters can be studied by placing virtual tunnels of differing customized shapes and sizes, experimentally into varying locations of the virtual 3-D models of the scanned bones. Examples of custom tunnel shapes include, though not limited to, tapered hole with precise depth control, keyhole, and chamferred hole. As current bone tunnel drilling is performed manually, bone tunnels today are limited only to simple cylindrical tunnels. With the advent of robotic surgery and the pre-op planning software described herein, custom tunnel shapes or sizes can be applied to improve bone tunnel placement. As shown in FIGS. 2B and 2C, the positioning and sizing in the tibia tunnel 22 and femoral tunnel 24 are optimized, respectively.

Figure 3:
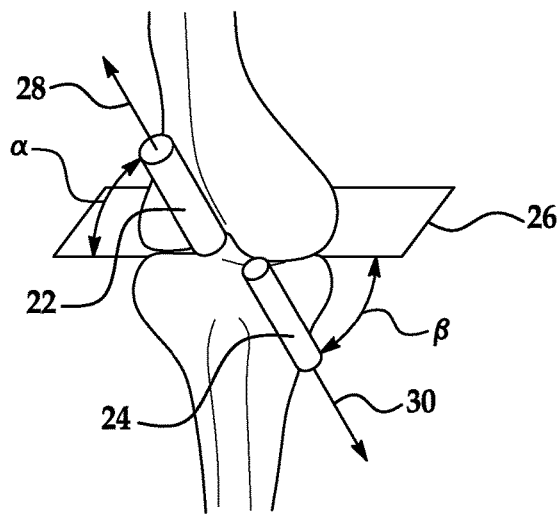
FIG. 3 shows a feature of the pre-operative tunnel placement software pre-determining the best fit axis and/or plane for matching multiple bone tunnels.

As shown in FIG. 3, the pre-op planning software may include visual placement guides inserted by the user such as virtual planes 26 and axes 28 and 30 to characterize optimal bone tunnel parameters. Best-fit algorithms may further be applied to prescribe the best location(s) and angle(s) alpha (α) and beta (β) of said planes and axes for a pair, or multiple, bone tunnels that interact spatially with one another. In this instance, for example in FIG. 3, the axis and plane generated by the best-fit algorithm show the position and angles of the tibial tunnel 22 and the femoral tunnel 24 are shown in exemplary from as being 60 degrees that will most optimally secure the ACL graft. By utilizing the pre-operative planning software described herein, surgical time to implant artificial ligament for ligament reconstruction will be reduced, particularly for the insertion of complex shaped ligament grafts.

Upon pre-determining the optimal bone tunnel parameters, either by the operator through the assistance of virtual bone tunnel modeling or by the best-fit plane-axis algorithm, this information is transmitted into an integration processor unit that couples the pre-operative planning software with a robotics system that performs precise and controlled bone evacuation. The integration processor unit is configured to communicate with the selected robotics system, such that the integration processor unit is able to create a set of instructions to drive the robotics system to create the bone tunnel precisely, according to the pre-determined optimal bone tunnel parameters, via a minimally invasive approach.

Figure 4A:
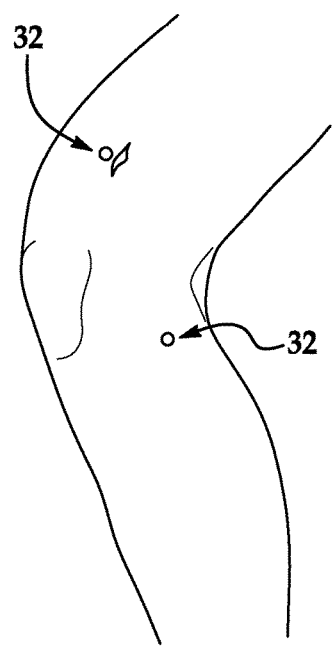
FIG. 4A shows the side view of a patient's knee with registration/recovery markers placed via small incisions.

FIG. 4A shows the side view of a patient's knee with registration/recovery markers 32 placed via small incisions. In some preferred embodiments, the registration/recovery markers 32 are placed percutaneously on the distal femur, and proximal tibia through incisions no larger than 2.5 centimeters. In some embodiments, registration/recovery markers 32 are not used.

Figure 4B:
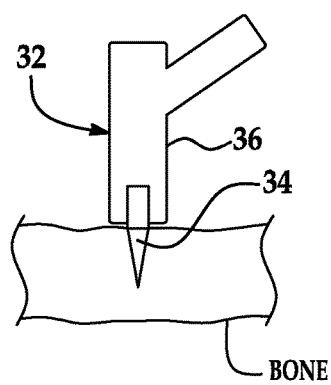
FIG. 4B shows the closed up cross-sectional side view of a registration/recovery post.

FIG. 4B shows the cross-sectional side view of a registration/recovery marker 32. As illustrated in FIG. 4B, the registration/recovery marker 32 includes an anchor distal member 34 and a removable proximal member 36. The anchor distal member 34 may be manually planted onto the target bone percutaneously. The anchor distal member 34 can be constructed with a traumatic distal segment to at least minimally pierce and press-fit onto the target bone. The anchor distal member 34 can be constructed with medical grade materials, such as though not limited to stainless steel, titanium, ABS, or polycarbonate. The removable proximal member 36 can be de-attached from the distal anchor member 34 once the anchor member is secured onto the desired bone. The removable proximal member 36 can be made from disposal materials such as but not limited to polypropylene, polyurethane, polycarbonate or ABS.

Figure 5:
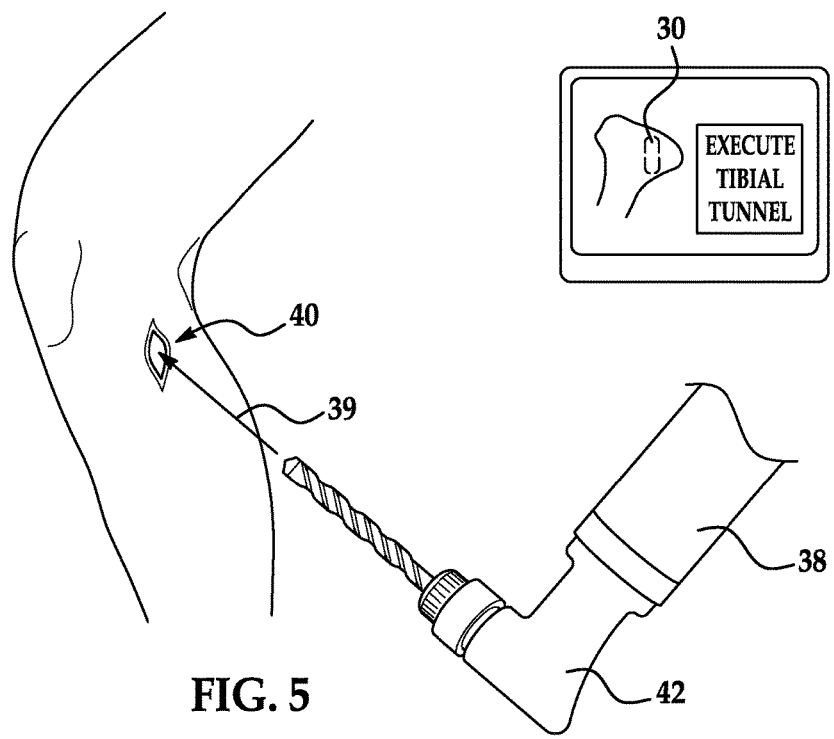
FIG. 5 shows the side view of a patient's knee with a robotic drill creating a tibia bone tunnel according to the pre-operatively determined tunnel parameters.

FIG. 5 shows the side view of a patient's knee with a robotic drill approaching the tibia bone tunnel according to pre-operatively determined tunnel parameters. To create the tibia bone tunnel 22, the robotic drill arm 38 is configured to first locate the planned position and path of the tunnel, and to align the drill axis 39 with the tibial tunnel axis 30, as shown in FIG. 3 and the inset simulative of a computer display. Next, an incision 40 is made by the robotic arm at the planned position to access the tibia bone. In some embodiments, the incision 40 may be about 5 centimeters long, however it is appreciated that any suitable incision size may be utilized. Upon confirmation with the pre-op planning software, the tibia bone tunnel 22 defined by the pre-determined tunnel parameters will be precisely executed by the robotic drill 42. Unlike manual drilling where the drill may slip or change direction due to non-homogenous bone structures or hard and slippery bone surfaces, the robotic cutting eliminates or greatly reduces these problems by the use of a high speed drill or burr, and the precision control thereof. During the cutting, the bone may be stabilized, fixed to the robot, or its location tracked in real time by bone motion monitors to increase precision.

Figure 6:
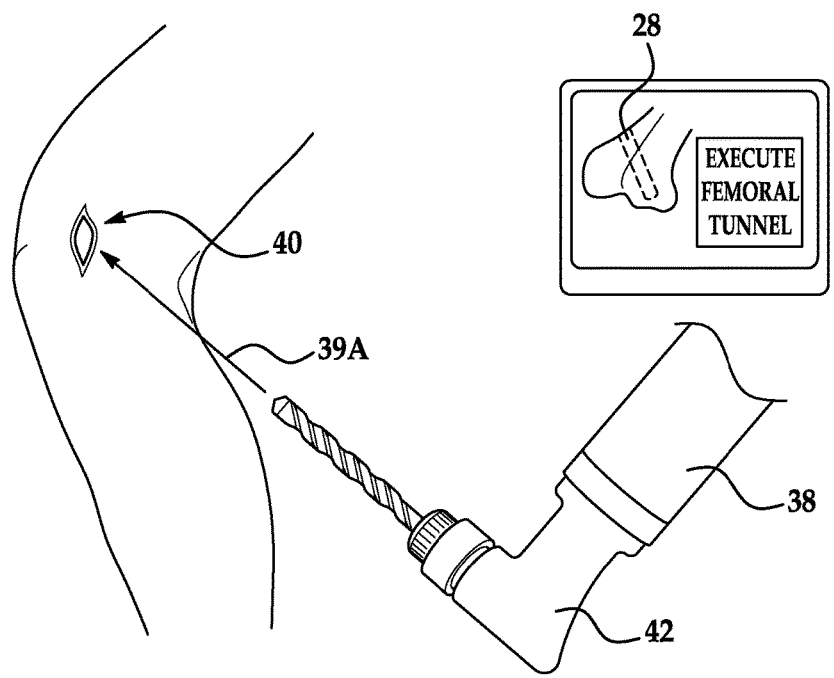
FIG. 6 shows the side view of a patient's knee with a robotic drill creating a femoral bone tunnel according to the pre-operatively determined tunnel parameters.

FIG. 6 shows the side view of a patient's knee with a robotic drill creating a femoral bone tunnel 24 according to pre-operatively determined tunnel parameters. Similar to the tibial tunnel 22, in some embodiments, location of the incision to access the femoral bone will be determined by the robotic drilling arm 38—through aligning the femoral tunnel axis 28 with the drill axis 39A, and by locating the position of planned tunnel 24, as shown in FIG. 3 and the inset simulative of a computer display. In some embodiments, an anteromedial portal (AMP) may be utilized, which is commonly used in ACL surgeries. Upon confirmation with the pre-op planning software, the femoral bone tunnel is executed by the robotic drill through the planned path and according to the pre-determined tunnel parameters minimally invasively. In some embodiments, the robotic bone tunnel placement for ACL reconstruction may be considered complete once the femoral and tibial tunnels are executed.

The applications of the disclosed invention discussed above are not limited to certain treatments or regions of the body, but may include any number of other treatments and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

Moreover, although in the previously described inventive embodiment, the placement of the tunnel has been pre-planned using a 3D model of the bone prior to the surgery, the preoperative planning of the tunnel placement can be performed based on one or more 2-D images, such as an X-ray.

In another inventive embodiment, the robotic drill may be used for tunnel placement without preoperative planning. In this embodiment, the surgeon may make an intra-operative decision on the placement of the tunnel, align the robotic drill in, and then use the robotic drill to assist in creating a controlled and precise cut within the bone.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

We claim:

1. A method for tunnel placement for ligament reconstruction in a subject comprising:
    receiving and processing scan data of a bone or a joint inclusive of the bone;
    then generating a three-dimensional virtual bone model of the bone;
    pre-determining a tunnel placement parameter with the virtual bone model; and
    then robotically creating a tunnel in the bone of the subject according to the pre-determined tunnel placement parameter adapted to receive a ligament graft.

2. The method of claim 1, wherein pre-determining the tunnel placement parameter is at least one of an optimal location or an optimal size.

3. The method of claim 1, wherein pre-determining the tunnel placement parameter further comprises creating at least one of a virtual axis or a virtual plane.

4. The method of claim 3, further comprising using software to generate best-fit angles of the virtual axis or the plane.

5. The method of claim 1, wherein a robotic system is creating the tunnel.

6. The method of claim 1, wherein a robotic system is creating the tunnel and includes the use of controlled drilling, heating or chemical method to create the tunnel.

7. The method of claim 1, wherein the joint is the knee and the tunnel is one configured for placement in femur or tibia for anterior cruciate ligament reconstruction.

8. The method of claim 1 further comprising placing a registration marker on the bone.

9. A system for tunnel placement for ligament reconstruction in a subject comprising:
    a processor to receive scan data of a bone or a joint inclusive of the bone, reconstruct a surface model of the bone or the joint and pre-determine at least one parameter of tunnel placement; and
    a surgical system having a plurality of moveable elements and coupled to the surface model to receive the at least one parameter, the surgical system configured to robotically create a bone tunnel according to the at least one parameter of tunnel placement, said tunnel adapted to receive a ligament graft.

10. The system of claim 9, wherein the processor is further configured to reconstruct the surface model of a femur bone, a tibia bone, or a knee joint, and pre-determine the at least one parameter of tunnel placement on the femur bone or the tibia bone.

11. The system of claim 9, wherein the processor is further configured to generate at least one of a virtual axis or a virtual plane.

12. The system of claim 9, wherein the processor is further configured to pre-determine at least one of tunnel placement parameter of location, size or angle.

13. The system of claim 9, wherein the tunnel is created by the surgical system by drilling, heating chemical methods or any combination thereof.

14. A method for tunnel placement for ligament reconstruction in a subject comprising:
    receiving intraoperative input from a surgeon to determine optimal tunnel placement parameters within a bone of the subject;
    restraining the movement of the bone relative to a surgical system of claim 9; and
    robotically creating one or more tunnels in the bone.

15. The method of claim 14, wherein the software determines an optimal location for tunnel placement based on a 3D virtual kinematic analysis of joint motion which may include optimizing range of motion and minimizing any impingement.

16. The method of 1 wherein, the virtual bone model is obtained by generating a three-dimensional (3-D) bone model from an image data set of the subject's bone.

17. The method of claim 16 wherein the image scan is a computed tomography (CT), dual-energy x-ray absorptiometry (DEXA), magnetic resonance imaging (MRI), X-ray scans, ultrasound, or a combination thereof.

18. The method of claim 1 further comprising aligning a robotic drill having a drill axis with a tunnel axis as defined by the pre-determined tunnel placement parameter prior to making an incision on the subject.

* * * * *